United States Patent [19]
Snyder et al.

[11] Patent Number: 5,923,775
[45] Date of Patent: Jul. 13, 1999

[54] APPARATUS AND METHOD FOR SIGNAL DEPENDENT NOISE ESTIMATION AND REDUCTION IN DIGITAL IMAGES

[75] Inventors: Patricia D Snyder, Pittsford; Thaddeus Francis Pawlicki, Rochester; Roger Stephen Gaborski, Pittsford, all of N.Y.

[73] Assignee: Eastman Kodak Company, Rochester, N.Y.

[21] Appl. No.: 08/822,722

[22] Filed: Mar. 24, 1997

Related U.S. Application Data

[60] Provisional application No. 60/014,863, Apr. 4, 1996.
[51] Int. Cl.$^6$ .............................. G06K 9/00; G06K 9/38; G06K 9/40
[52] U.S. Cl. .......................... 382/172; 382/168; 382/261
[58] Field of Search ..................................... 382/260, 261, 382/264, 275, 205, 266, 132, 168, 172, 254, 199, 270, 274

[56] References Cited

U.S. PATENT DOCUMENTS

| | | | |
|---|---|---|---|
| 5,091,972 | 2/1992 | Kwon et al. | 382/277 |
| 5,533,149 | 7/1996 | Kaplan et al. | 382/260 |
| 5,563,963 | 10/1996 | Kaplan et al. | 382/266 |
| 5,724,454 | 3/1998 | Shimazu et al. | 382/258 |
| 5,764,307 | 6/1998 | Ozcelik et al. | 348/608 |

FOREIGN PATENT DOCUMENTS 0 524 969  12/1993  European Pat. Off. ........ G06F 15/68

OTHER PUBLICATIONS

Ballard, D.H. and Brown, C.M., Computer Vision, Prentice Hall, 1982, pp. 76–78.

Abdou, I.E., "Quantitative Methods of Edge Detection," USCIPI Report 830, Image Processing Institute, University of Southern California, Jul. 1978.

Olsen, S.I., "Estimation of Noise in Images: An Evaluation," CVGIP: Graphical models and Image Processing, vol. 55, No. 4, Jul. 1993, pp. 391–323.

Lee, J.S. "Refined Filtering of Image Noise Using Local Statistics, ", Computer Vision Graphics Image Processing, 15, 1981, pp. 380–389.

Mastin, G.A., "Adaptive Filters for Digital Noise Smoothing, and Evaluation," Computer Vision Graphics and Image Processing, 31, 1985, pp. 103–121.

Meer, P., Jolion, J., and Rosenfeld, A., "A Fast Parallel Algorithm for Blind Estimation of Noise Variance," IEEE Trans. Pattern Anal. mach. Intelligence, 12(2), 1990, pp. 216–223.

*Primary Examiner*—Leo H. Boudreau
*Assistant Examiner*—Dmitry A. Novik
*Attorney, Agent, or Firm*—William F. Noval

[57] ABSTRACT

The present invention efficiently and quickly estimates signal (code value) dependant noise in an image and subsequently reduces that noise. The digital image is segmented both according to code value and into smooth vs. textured regions. Noise estimates taken from smooth regions are used to model noise as a function of code value. The predictions of the model are used to tone noise reduction in all areas of the image according to the appropriate code value.

4 Claims, 7 Drawing Sheets

APPARATUS AND METHOD FOR SIGNAL DEPENDENT NOISE ESTIMATION AND REDUCTION IN DIGITAL IMAGES

CROSS REFERENCE TO RELATED APPLICATION

Reference is made to and priority claimed from U.S. Provisional Application Ser. No. U.S. 60/014,863, filed Apr. 4, 1996, entitled APPARATUS AND METHOD FOR SIGNAL DEPENDENT NOISE ESTIMATION AND REDUCTION IN DIGITAL IMAGES.

FIELD OF INVENTION

This invention is broadly directed to the field of image data processing and image acquisition systems. A primary application of the invention relates to the processing of x-ray images.

BACKGROUND OF INVENTION

Images acquired from many imaging devices usually contain noise. This noise can adversely impact the perception of such images and distort the effect of subsequent image processing steps. Many systems can produce signal dependent noise. In medical x-ray imaging, there exists a direct trade-off between patient exposure and image quality. The desire to maintain lower exposure dosages results in more noise present in the image. It is, therefore, beneficial to reduce the amount of noise subsequent to image acquisition.

The present application is related to U.S. Pat. No. 5,091,972, entitled "System and method for Reducing Digital Image Noise", by Kwon et. al. dated Feb 25, 1992. It is also related to U. S. patent application Ser. No. 399,134 filed on Aug. 28, 1989, entitled "Digital Image Noise REduction of Luminance and Chrominance base on Overlapping Planar Approximation", by Kaplan et. al. and U.S. patent application Ser. No. 07/399,135 filed on Aug. 28, 1989, entitled "A Computer Based Digital Image Noise Reduction Method Based on Overlapping Planar Approximation" by Kaplan et. al. The techniques described by Kaplan and Kwon have two major drawbacks which are overcome by the invention presented in this disclosure. The first drawback relates to estimating the precise amount of noise to be expected.in an image. These previous techniques require an a priori estimate of the noise present in the image. In practice, such estimates are derived through laborious calibration and measurement of the particular imaging system used in the application. Our technique estimates the noise on each image input to the system. As such, it is not particular to any particular imaging system. The second drawback relates to the fact that these techniques use a single signal-independent estimate for noise across the entire dynamic range of the image. Our technique differentially estimates and removes noise as a signal-dependent function of image the image features themselves

SUMMARY OF THE INVENTION

An object of this invention is to provide a system for estimating and reducing noise in images.

The invention has two stages. The first is the estimation of the signal dependent noise in the image. The second is the signal dependent noise reduction through image processing based on the estimates obtained from the first stage. For each of the pixels in the original image, an estimate of the 2-D gradient is calculated.

The noise estimating technique described provides a signal dependent noise characterization of the image. To do this the image is segmented into a plurality of images. Each of the new images represents a certain range of code values found in the original image. Each of the new images contains only those pixels with code values in the range represented by the new image.

For each of the images in the plurality of new images the corresponding pixels in the gradient image are examined. A histogram of gradient values is calculated for each image in the plurality of new image. These histograms are used to determine a gradient threshold point for each range of code values in the original image.

For pixels in the original image, if the said threshold criterion corresponding to that pixel's code value range is met, then an expected value is computed for that pixel. The difference between the expected and the actual code value is then calculated. For each code value range, the standard deviation of the difference between the expected and real difference is calculated. The standard deviation is used as the estimate of noise for that code value range. For the second stage (noise reduction) a plurality of expected values are calculated for each pixel in the original image. A different neighborhood of pixels is used to generate each of the plurality of expected values. The difference between the actual pixel code value and each of the expected values is also calculated. A new estimate of the pixel's code value is derived by aggregating all of the plurality of expected values. Expected values with lower differences are weighted higher than those with higher differences and all estimates are adjusted by the signal dependent amount of noise estimated in the first stage. Thus, a new estimated code value is generated for each pixel in the original image. All of these new estimates, together, create a new noise reduce image.

BRIEF DESCRIPTION OF THE DRAWINGS

The preferred modes of the invention are described in detail with reference to the accompanying drawings, of which.

DETAILED DESCRIPTION OF THE PREFERRED EMBODIMENTS

Figure 1:
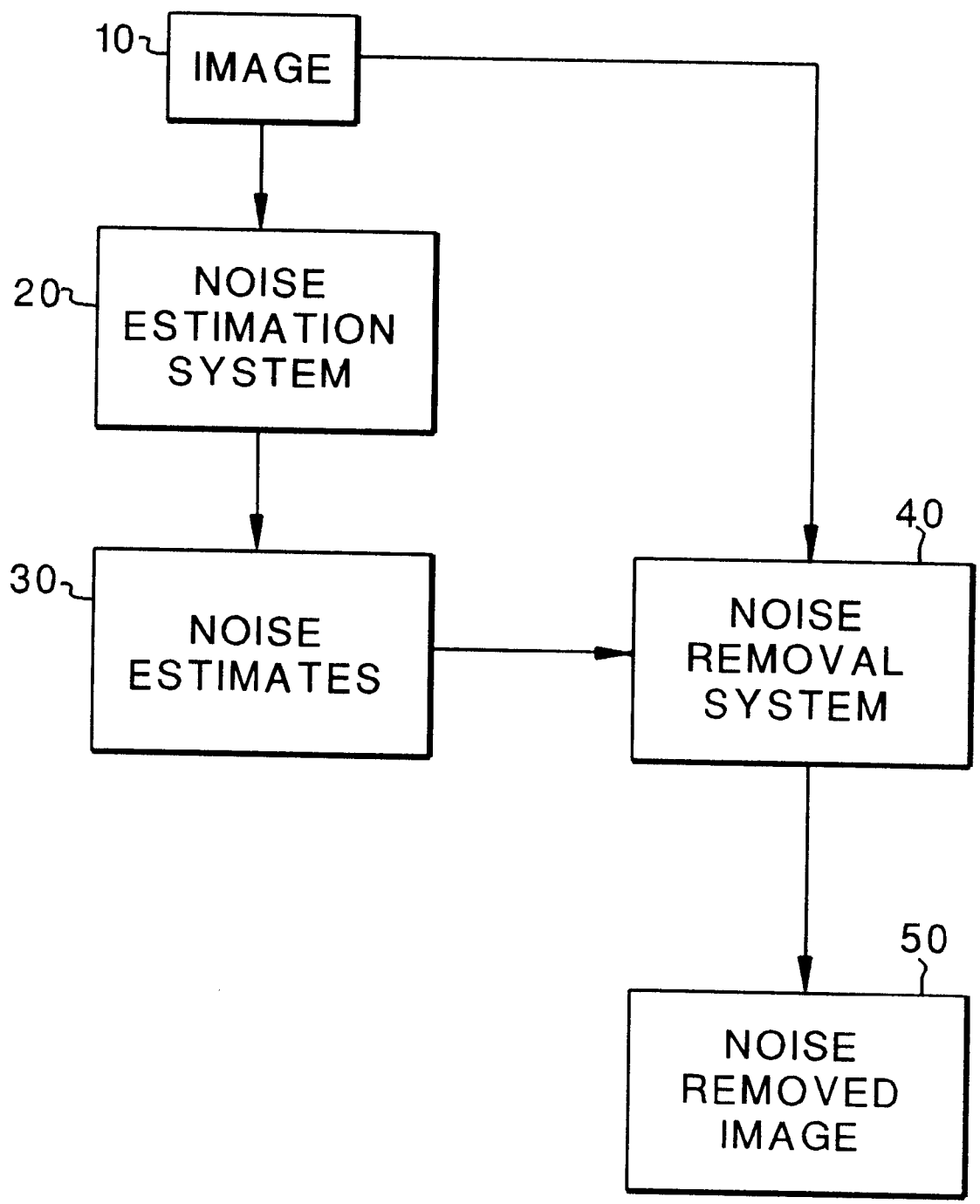
FIG. 1 is as simplified block diagram illustrating the overall system embodying the invention; Block 10 represents the digital image or signal input to the system. Block 50 represents the ultimate product output from the system: an image with lower noise than the input image.

The invention disclosed here reduces noise in digital images. A high level illustration of the system realizing the invention is depicted in FIG. 1. The input to the system is a digital image or signal (Block 10). The output or end result of the invention is a noise reduced version of the input image (Block 50). This process is conceptualized as a two stage process. The first stage being that of Noise Estimation (Block 20) The Noise Estimation System generates an intermediate result consisting of a plurality of Noise Estimates (Block 30). The second stage is that of Noise Removal (Block 40). Signal dependent image noise standard deviation is computed using the following approach.

Figure 2:
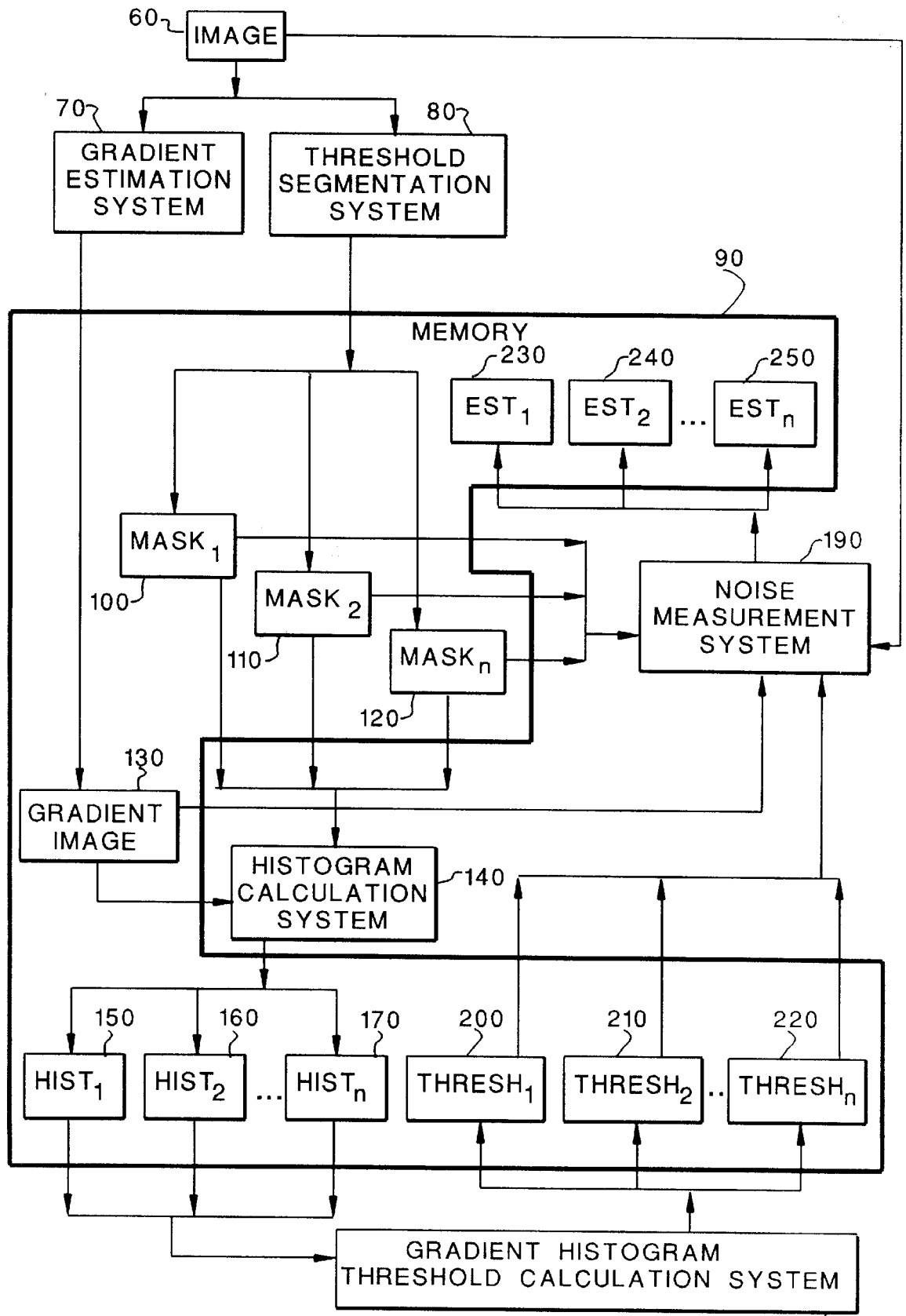
FIG. 2 illustrates the first stage (noise estimation) of the invention. This figure represents a detailed illustration of the Noise Estimation System from Block 20 from FIG. 1. Block 60 represents the digital image or signal input to the system. Blocks 230, 240, and 250 represents the ultimate product output from the system: a plurality of scalar estimates of the noise present in each code value band selected from the input image

The Noise Estimation System referred to FIG. 1 is depicted in FIG. 2. The input image or signal (Block 50 in FIG. 1, represents the same entity as Block 60 in FIG. 2), is the initial input to the system. This input image or signal is processed by a Gradient Estimation System (Block 70) in order to generate a Gradient Image (Block 130). The Gradient Image represents the magnitude of the gradient at each point in the image, independent of direction. Many methods of calculating this gradient magnitude are known in the literature. [1]

1. Ballard, D. H. and Brown, C. M. *Computer Vision*, Prentice Hall, 1982. pp 76–78. The preferred method is to convolve the image with the well known Prewitt operators. [2]
2. Abdou, I. E. "Quantitative methods of edge detection." USIP Report 830, Image Processing Institute, Univ. Southern Calif., July, 1978.

The input image or signal (Block 60) is also processed by a Threshold Segmentation System (Block 80) in order to produce a plurality of Mask Images (Blocks 100, 110, and. 120). Although FIG. 2 shows three such masks, several more are used in the preferred embodiment. The precise number use in practice is application dependent. In the preferred embodiment, a histogram of code values is generated from the region of interest of the image. In some applications, the region of interest will include the entire input image. In x-ray imaging application, the region of interest usually includes only the body part under consideration. The code value range of the image's region of interest is calculated and partitioned the dynamic range of the region of interest into N, where N a positive integer, equal sub-intervals by considering the histogram.

The Histogram Calculation System (Block 140) independently processes each of the Mask Images (Blocks 100, 110 . . . 120) with the Gradient Image (Block 130). For each sub-interval represented by a Mask Image, a Histogram of the gradient magnitude is calculated. This results in a plurality of Histograms (Blocks 150, 160, . . . , 170), There is a one to one correspondence between the Histograms and the Mask Images.

Each of the plurality of Histograms (Blocks 150, 160, . . . , 170) is independently processed by a Gradient Histogram Threshold Calculation System (Block 180) resulting in a plurality of scalar Thresholds (Blocks 200, 210, . . . , 220). The plurality of Histograms depicted in Blocks 150, 160, . . . , 170 of FIG. 2 represent the same entities as the plurality of Histograms depicted in Blocks 620, 630, . . . , 640 of FIG. 5. Similarly, the plurality of scalar Thresholds depicted in Blocks 200, 210, . . . , 220 of FIG. 2 represent the same entities as the plurality of Thresholds depicted in Blocks 750, 760, . . . , 7700 of FIG. 5. The whole of FIG. 5 illustrates a detailed view of the Gradient Histogram Threshold Calculation System (Block 180) in FIG. 2.

Figure 5:
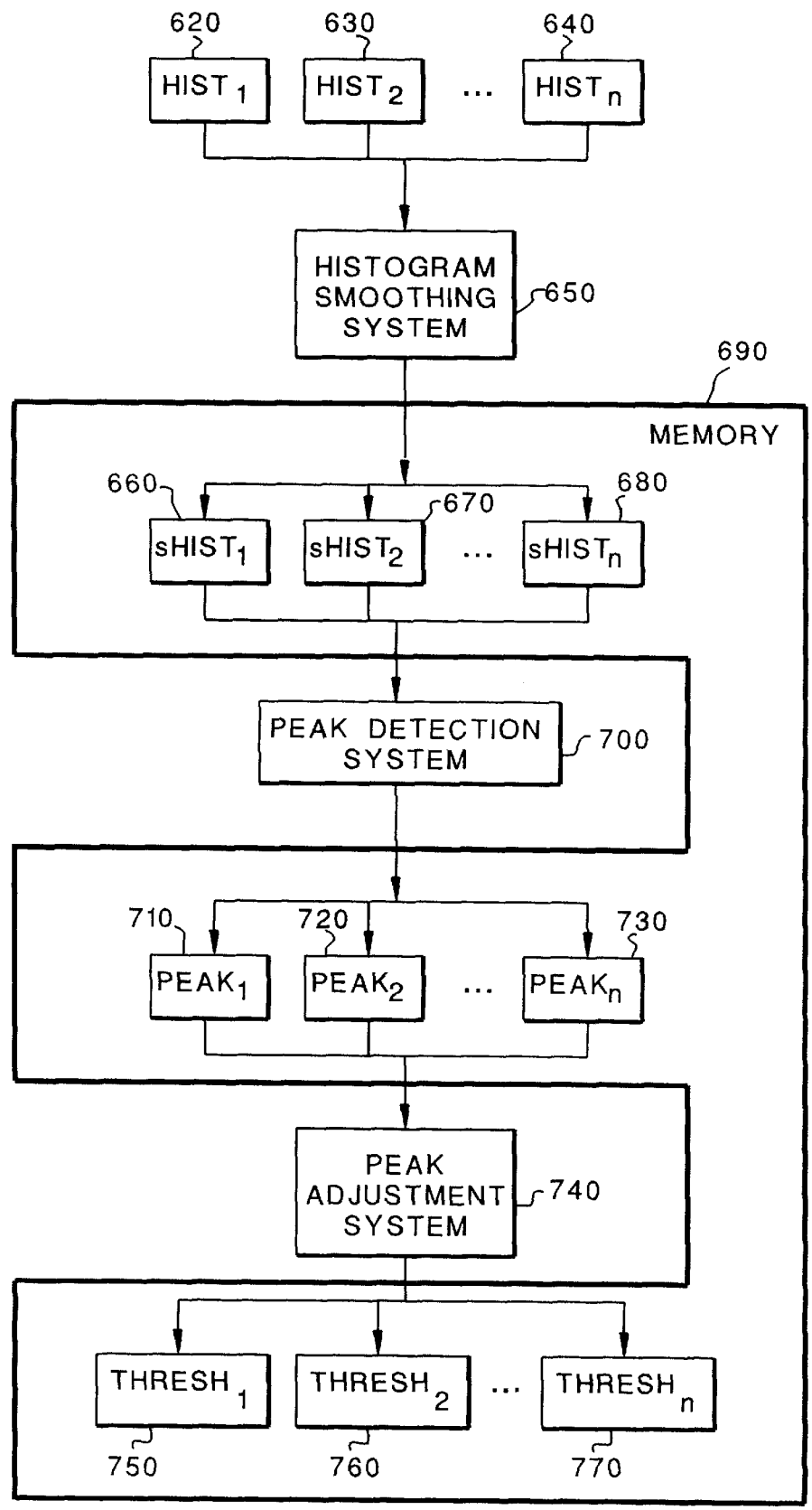
FIG. 5 is a simplified block diagram representing a detailed illustration of the Gradient Threshold Calculation System (Block 180 from FIG. 2).

As illustrated by the simplified block diagram of FIG. 5, the plurality of Histograms (Blocks .620, 630, . . . , 640) are each processed, for robustness, by a Histogram Smoothing System (Block 650) resulting in a plurality of smoothed histograms (Blocks 660, 670, . . . , 680). Many techniques of signal smoothing are widely known in the literature. The preferred embodiment smooths using a gaussian filter. In turn, the plurality of smoothed histograms (Blocks 660, 670, . . . , 680) are each processed by a Peak Detection System (Block 700) resulting in a plurality of scalar Peak locations (Blocks 710, 720, . . . , 730). In the current preferred embodiment, the peak of each gradient histogram is the gradient magnitude value which contains the highest pixel count in the smoothed histogram. Each Peak (Blocks 710, 720, . . . , 730) is processed by a peak adjustment system resulting in a plurality of scalar Thresholds (Blocks 750, 760, . . . , 770). In the preferred embodiment, two-thirds of the peak value is used as the threshold value.

Figure 4:
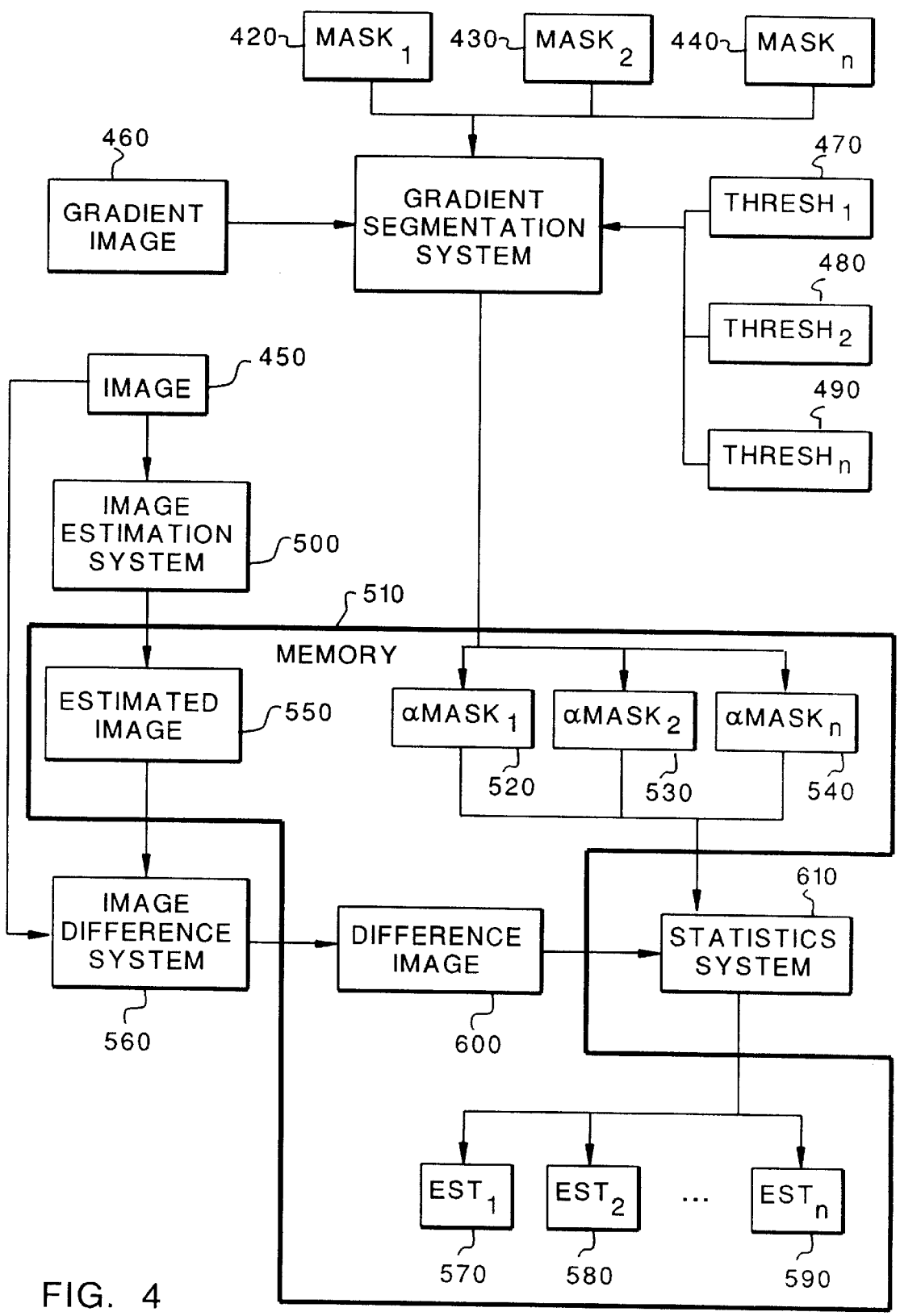
FIG. 4 is a simplified block diagram representing a detailed illustration of the Noise Measurement System (Block 190 from FIG. 2).

The Noise Measurement system (Block 190) seen in FIG. 2 is illustrated in greater detail in FIG. 4. The input Image depicted by Block 450 in FIG. 4 represents the same entity as Block 10 in FIG. 1 and Block 60 in FIG. 2. The gradient Image depicted by Block 460 in FIG. 4 represents the same entity as Block 130 in FIG. 2. The plurality of Mask Images (Blocks 420, 430, . . . , 440) in FIG. 4 represent the set of entities by the same name (Blocks 100, 110, . . . , 120) in FIG. 2. Similarly The plurality of scalar Thresholds (Blocks 470, 480, . . . , 490) in FIG. 4 represent the set of entities by the same name (Blocks 200, 210, . . . , 220) in FIG. 2, and FIG. 5 (Blocks 750, 760, . . . , 770).

The Gradient Image (Block 460) along with the plurality of Mask Images (Blocks 420, 430, . . . , 440), and the Plurality of scalar Thresholds (Blocks 470, 480, . . . , 490) are processed together by a Gradient Segmentation System (Block 470) resulting in a new set of Mask Images which are referred to as αMasks (Blocks 520, 530, . . . , 540) in FIG. 4. In the preferred embodiment, for each Mask Image, the Gradient Segmentation System (Block 470) examines each pixel in the gradient Image (Block 460) present in the Mask Image and compares the value of the gradient image pixel to the scalar threshold value corresponding to that Mask Image. (e.g. Block 420 corresponds to Block 470, Block 430 to Block 480, and Block 440 to Block 490). For each pixel, if the magnitude of the gradient is less than the threshold value, the expected value at that pixel is included in the corresponding αMask Image.

The input image (Block 450) is processed by an Image Estimation System (Block 500) to produce an Estimated Image (Block 550). In the preferred embodiment, a 3×3 window is used to calculate the expected value. A least squares linear fit is computed as the expected code value. This calculation is simplified by the fact that for an odd number of points, the center value is equal to the average of these points.

Both the Input Image (Block 450) and the Estimated Image (Block 550) are together processed by a Image DIfference System (Block 560) to produce a Difference Image (Block 600). In the preferred embodiment, the difference between the image code value and the expected value is calculated using standard image subtraction.

For each of the plurality of Mask images (Blocks 520, 530, ..., 540), the relevant pixels in the Difference Image (Block 600) are operated on by a Statistics System (Block 610). Resulting in a plurality of Noise Estimates (Blocks 570, 580, ..., 590). In the preferred embodiment, the Estimates represent the standard deviation of the relevant pixels in the Difference Image corresponding to each αmask. In the preferred embodiment, the Statistics system keeps a count of the number of pixels used to calculate each noise measure estimate in order to ensure statistical significance associated with the particular sub-interval. If this count is less than that which is considered statistically significant, the sub-interval is combined with an adjacent sub-interval.

Figure 3:
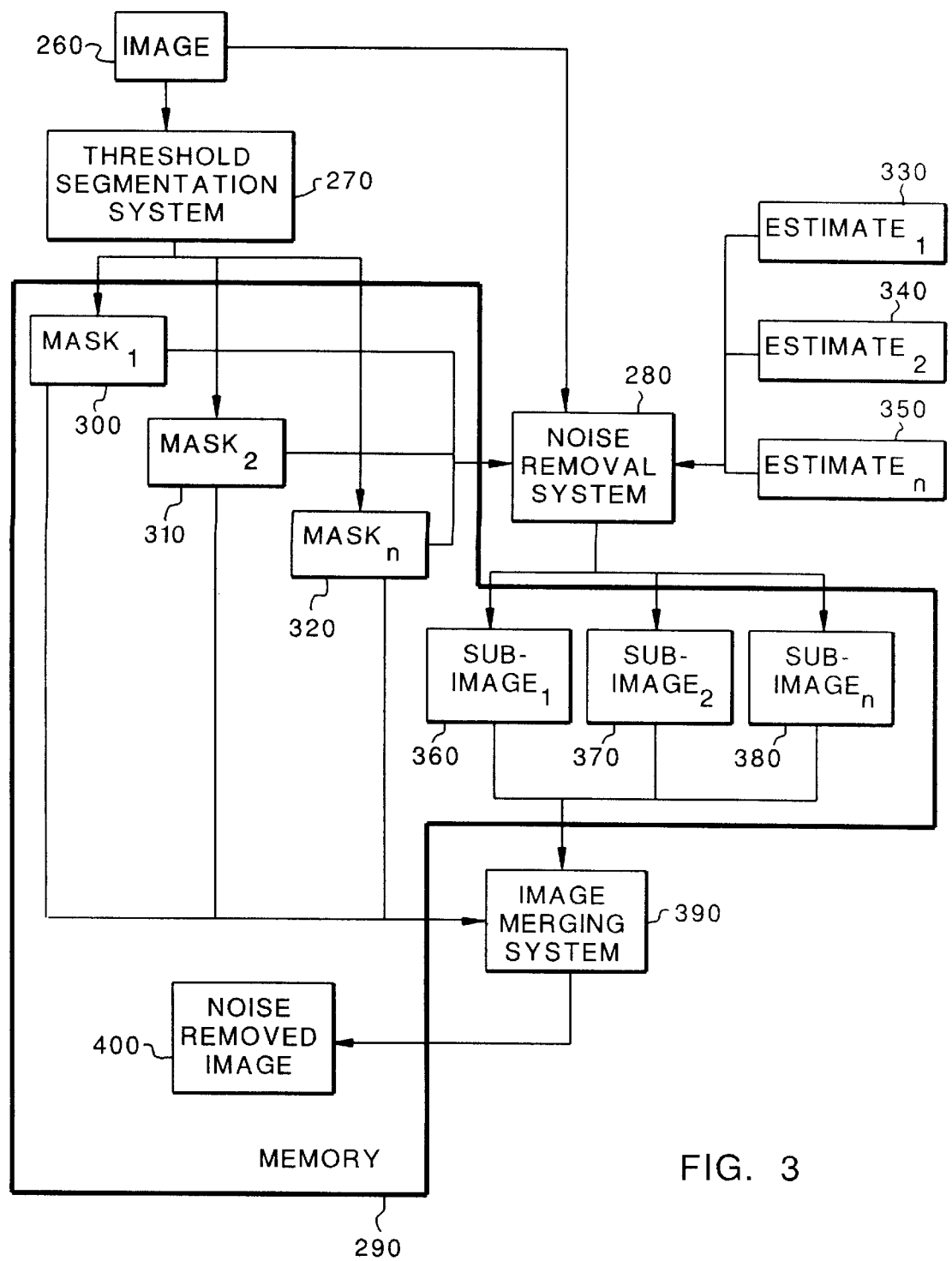
FIG. 3 illustrates the second stage (noise removal) of the invention. This figure represents a detailed illustration of the Noise Removal System from Block 40 from FIG. 1. Block 260 represents the digital image or signal input to the system. Blocks 330, 340, and 350 represent the plurality of estimates generated in at the output of the first stage. These estimates represent the same entities as Blocks 230, 240, and 250, in FIG. 2 and Block 30 in FIG. 1. Block 400 represents the ultimate product output from the system: an image with lower noise than the input image, which is the same entity represented in Block 50 of FIG. 1.

The second stage of the invention is termed a Noise Removal System (Block 40, FIG. 1). The second stage uses both the Input Image (Block 10) and the plurality of Noise Estimates (Block 30) generated during the first stage. The processing of the second stage results in the final product output by the invention: a Noise Removed Image (Block 50). FIG. 3 is a simplified block diagram illustrating the second stage of the invention, a detailed depiction of the Noise Removal System (Block 40).

The Input Image (Block 260, FIG. 3) is processed by a Threshold Segmentation System (Block 270) to generate a plurality of Mask Images (Blocks 300, 310, ..., 320). This process is similar to the process described above in the first stage and depicted in Block 80 of FIG. 1. However, the actual number of Mask images used is independent of the number used in the first stage. In practice, it is possible and optimal to have a separate mask for each possible quantized value in the dynamic range of the input image. This is possible if Noise Estimate values can be generated for the additional code value bands. In practice, it is possible to generate such new values. Additional signal dependent noise estimates can be calculated by linear interpolation, or by fitting an exponential model to the data, or by any other model that may be appropriate.

The Input Image (Block 260) is processed with the plurality of Mask Images (Blocks 300, 310, ..., 320) and their corresponding Noise Estimates (Blocks 330, 340, ..., 350), by a signal independent Noise Removal System (Block 280) to generate a plurality of noise removed Sub-Images (Blocks 360, 370, ..., 380). The preferred embodiment of the invention uses a signal independent, multiple neighborhood, Overlapping Planar Approximation Systems. The Plurality of noise removed sub-Images (Blocks 360, 370, ..., 380) are then processed by an Image Merging System (Block 390) resulting in the final product output by the invention: a Noise Removed Image (Block 400 FIG. 3, represents the same entity as Block 50 FIG. 1).

1. U.S. Pat. No. 5,091,972, "System and Method for Reducing Digital Image Noise", Feb. 25, 1992. Assignee Eastman Kodak Company.

Novelty and Advantages over the Prior Art

Vuylstege[2] attempts noise reduction through the decomposition of an image into a sequence of detail images and attenuating through the locally estimated amount of signal with an estimated noise level. His technique is computationally expensive since it requires a complex pyramidal multi-resolution decomposition processing and reconstruction of the image. The invention presented in this disclosure has the advantage of computational efficiency. Even though a plurality of masks are generated in the presented invention, the pixels present in one mask are not present in any other mask. Vuylstege's approach also uses a global estimate of noise, our invention uses a noise estimate which is a function of image code value.

2. European Patent Publication No. 0-574-969-A2, "A method and apparatus for noise reduction". Vuylstege, P., Dated: May. 19, 1993. Olsen [3] experimentally evaluated several methods of Noise estimation in images. All methods-measured noise in terms of the standard deviation of white additive noise in images. All 3. Olsen, S. I., "Estimation of Noise in Images: An Evaluation." CVGIP: Graphical Models and Image Processing, Vol. 55, No. 4, July, pp. 391–323, 1993. of these methods were signal independent. Lee [1] , used spatially adaptive noise estimation which was not dependant on code value. Mastin [2] used a similar signal independent approach. Meer et. al. [3] extended this approach by iterative selection from among the smallest variances in sequences of image blocks.None of these methods adjusted or evaluated noise as a function of the pixel code value, as the present invention does.

1. Lee, J. S., "Refined filtering of image noise using local statistics", Computer Vision Graphics Image PRocessing, 15, 1981, 380–389.
2. Mastin, G. A., "Adaptive filters for digital noise smoothing, and evaluation". Computer Vision Graphics and Image Processing, 31, 1985, 103–121.
3. Meer, P., Jolion, J., and Rosenfeld, A., "A fast parallel algorithm for blind estimation of noise variancen", IEEE Trans. Pattern Anal. Mach. Intelligence, 12 (2), 1990, 216–223.

Figure 6:
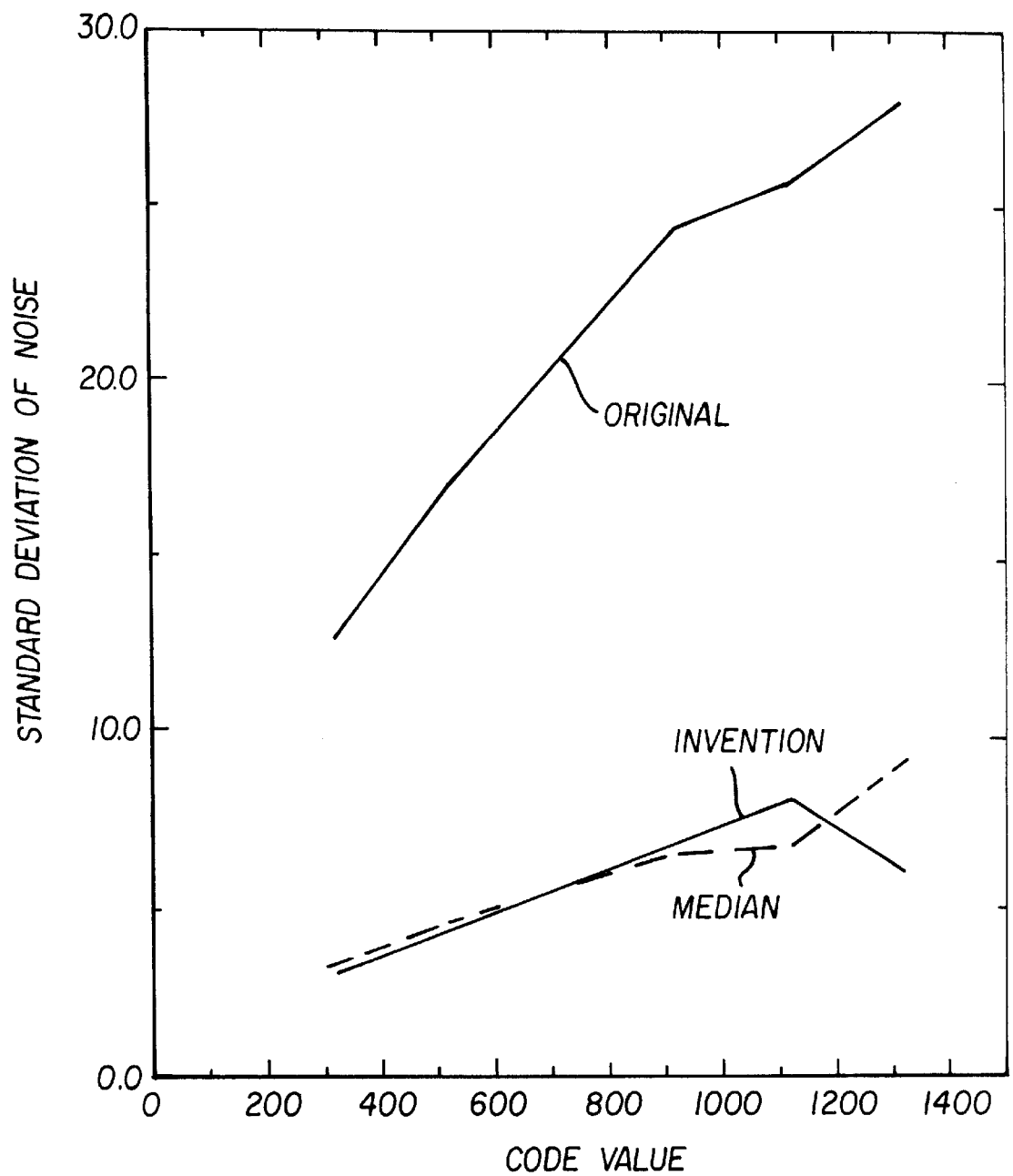
FIG. 6 is a graph showing the measured noised comparison of the invention to median filtering. Equal noise deduction can be achieved.
Figure 7:
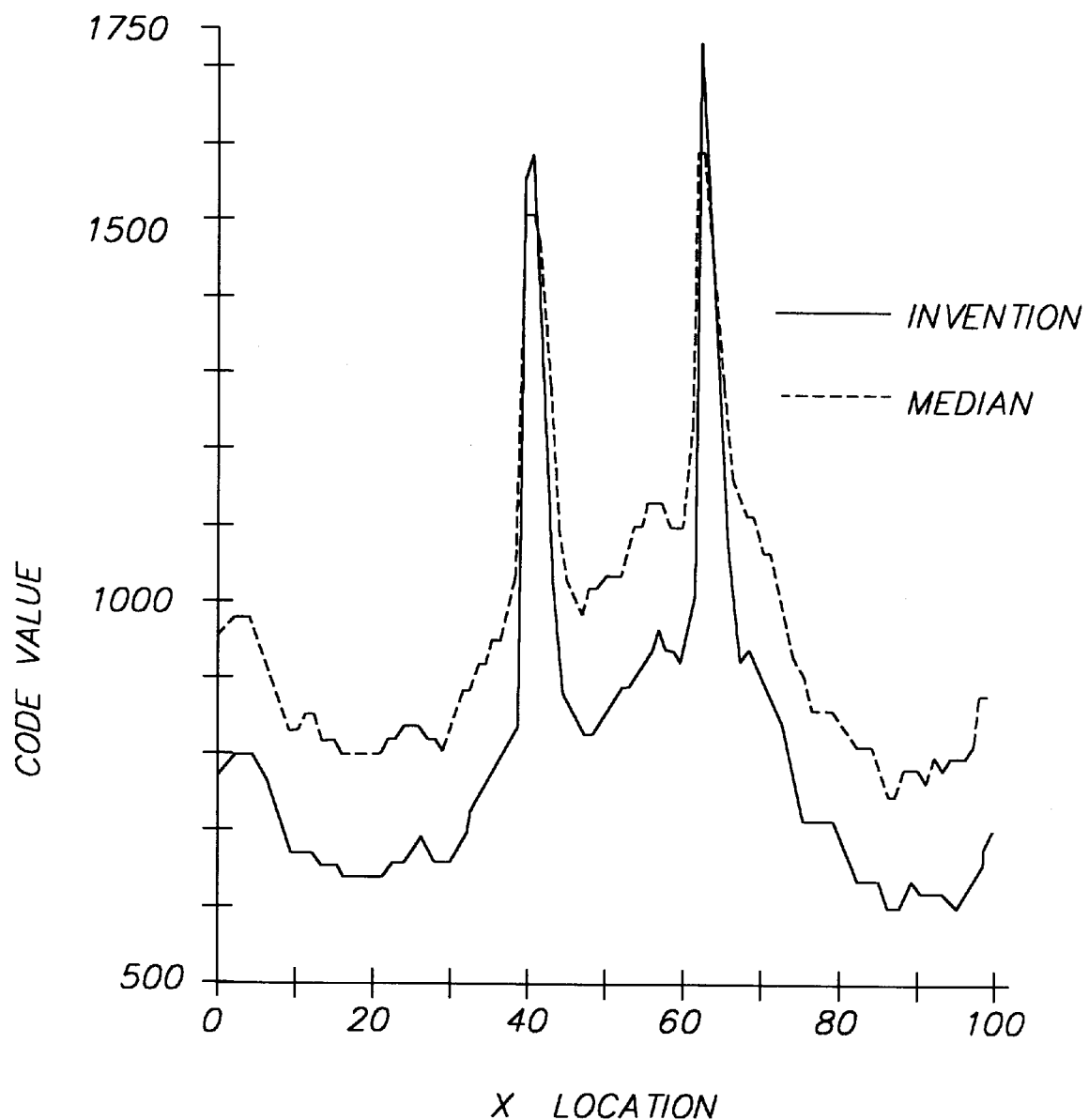
FIG. 7 is a graphical comparison of the invention to median filtering. For the equal amount of noise reduction, the invention shows greater detail.

The techniques described by Kwon[4] and Kaplan[5,6] have addressed signal independent noise reduction using an overlapping planar approximation attenuated by estimated noise levels in the image. The preferred embodiment uses this technique. There approach contains two major drawbacks which are overcome by the invention presented in this disclosure. The first drawback relates to estimating the precise amount of noise to be expected in an image. These previous techniques require an a priori estimate of the noise present in the image. In practice, such estimates are derived through. laborious calibration and measurement of the particular imaging system used in the application. Our technique estimates the noise on each image input to the system. As such, 4. U.S. Pat. No. 5,091,972, entitled "System and method for Reducing Digital Image Noise", by Kwon et. al. dated Feb 25, 1992.
5. U.S. patent application Ser. No. 399,134 filed on Aug. 28, 1989, entitled "Digital Image Noise Reduction of Luminance and Chrominance base on Overlapping Planar Approximation", by Kaplan et. al. it is not particular to any particular imaging system. The invention disclosed here has the capability of performing a blind estimation before processing for noise reduction. The second drawback relates to the fact that these techniques use a single signal-independent estimate for noise across the entire dynamic range of the image. Our technique differentially estimates and removes noise as a signal-dependent function of image the image features themselves FIG. 6 graphically depicts the measured noise in an original mammographic x-ray image, that of the image processed by the invention, and that of the image processed by a median filtering technique. It can be seen that equal amounts of noise reduction can be achieved by either method. However, FIG. 7 shows a graphical view of a scan line through micro-calcifications in a significant region of interest in the mamogram processed by the two techniques. It can be clearly seen that for equal amounts of noise reduction, the technique presented in the invention maintains greater detail. Features such as these are one of the earliest indicators of disease in mammograms. It is imperative, therefore, that any noise reduction technique maintain visibility of these types of features. The invention, therefore, has a clear advantage over the standard technique in terms of retaining detail while reducing noise.

We claim:

1. A method for noise estimation and reduction in digital images comprising the following steps:

providing a digital image having a range of code values and having signal dependent noise;

measuring signal dependent noise in said digital image (FIG. 1 Block 10), with a Noise Estimation System (20) which calculates a noise standard deviation estimate corresponding to each code value found in said digital image;

using said noise estimates (30) to configure a Noise Removal System (40);

processing said digital image (10) with the above configured Noise Removal System (40) in order to generate a Noise Reduced Version of said digital image (50).

2. A method to Estimate Signal Dependent Noise in Images (20) comprising the following steps:

providing a digital image having signal dependent noise;

processing said digital image (10,60) with a Gradient Estimation System (FIG. 2, Block 70), in order to generate a Gradient Image (130), and storing said Gradient Image in Memory (90);

processing said Gradient Image (60) with a Threshold Segmentation System (80), in order to generate a plurality of Mask Images (100, 110, . . . , 120), each representing a specific range of pixel code values in said digital image (60), and storing said Mask Images in memory (90); processing said Gradient Image (130) with each of the plurality of Mask Images (100, 110, . . . , 120), in order to generate a plurality of Histograms (150, 160, . . . , 170), and storing said histograms in memory (90);

processing the plurality of said Histograms (150, 160, . . . , 170) through a Gradient Histogram Threshold Calculation System (180) in order to generate a plurality of scalar Thresholds (200, 210, . . . , 220) and storing said scalar Thresholds in memory (90); and processing said digital image (60), the plurality of Mask Images, and the plurality of scalar Thresholds with a Noise Measurement System (190) in order to generate a plurality of Signal Dependent Noise Estimates (230, 240, . . . , 250), each Signal Dependent Noise Estimate corresponding to a specific band of code values in said digital image (60), and storing said Signal Dependent Noise Estimates in memory (90).

3. The method of claim 2 wherein processing with a Noise Measurement System step includes the following steps:

the Gradient Image, the plurality of Mask Images, and the plurality of Scalar Thresholds are processed together by a gradient segmentation system to produce a new set of Mask Images and Masks;

the digital image is processed by an image estimation system to produce an estimated image;

the digital image and the estimated image are processed together by an image difference system to produce a difference image including relevant pixels; and for each member of the new set of Mask Images, the relevant pixels in the difference image are operated on by a statistics system to produce a plurality of noise estimates.

4. The method of claim 2 wherein said Gradient Histogram Threshold Calculation System includes the steps of:

each of said plurality of histograms is processed for robustness by a histogram smoothing system to produce a plurality of s smoothed histograms;

each of said histograms is processed by a peak detection system to produce a plurality of scalar peak locations;

each scalar peak location is processed by a peak adjustment system to produce said plurality of scalar thresholds.

* * * * *